US011719676B2

(12) United States Patent
Hill

(10) Patent No.: US 11,719,676 B2
(45) Date of Patent: Aug. 8, 2023

(54) MACHINE LEARNING MONITORING AIR QUALITY

(71) Applicant: David Alexander Hill, Aspen, CO (US)

(72) Inventor: David Alexander Hill, Aspen, CO (US)

(73) Assignee: David Alexander Hill, Aspen, CO (US)

( * ) Notice: Subject to any disclaimer, the term of this patent is extended or adjusted under 35 U.S.C. 154(b) by 281 days.

(21) Appl. No.: 17/221,741

(22) Filed: Apr. 2, 2021

(65) Prior Publication Data

US 2021/0311008 A1    Oct. 7, 2021

Related U.S. Application Data

(60) Provisional application No. 63/074,330, filed on Sep. 3, 2020, provisional application No. 63/004,023, filed on Apr. 2, 2020.

(51) Int. Cl.
*G01N 33/00* (2006.01)
*G06N 20/00* (2019.01)

(52) U.S. Cl.
CPC ..... *G01N 33/0063* (2013.01); *G01N 33/0075* (2013.01); *G06N 20/00* (2019.01); *G01N 2033/0068* (2013.01)

(58) Field of Classification Search
CPC . G01N 33/0063; G01N 33/0075; G06N 20/00
USPC ....................................................... 340/632
See application file for complete search history.

(56) References Cited

U.S. PATENT DOCUMENTS

| | | | | |
|---|---|---|---|---|
| 6,919,809 | B2 * | 7/2005 | Blunn | F24F 11/61 340/532 |
| 10,309,668 | B2 * | 6/2019 | Song | F24F 3/0442 |
| 2006/0174560 | A1 * | 8/2006 | Levine | F24F 13/32 52/200 |
| 2006/0234621 | A1 * | 10/2006 | Desrochers | G01N 1/26 702/50 |
| 2009/0143915 | A1 * | 6/2009 | Dougan | F24F 11/0001 454/229 |
| 2011/0046790 | A1 * | 2/2011 | Miller | G05B 19/05 700/295 |
| 2012/0232702 | A1 * | 9/2012 | Vass | G05D 23/1934 700/277 |
| 2013/0085613 | A1 * | 4/2013 | Bester | F24F 11/58 165/59 |
| 2017/0122610 | A1 * | 5/2017 | Lazar | F24F 11/30 |
| 2019/0137156 | A1 * | 5/2019 | Popli | F25B 49/022 |

(Continued)

*Primary Examiner* — Kerri L McNally
(74) *Attorney, Agent, or Firm* — Mughal Gaudry & Franklin PC

(57) ABSTRACT

A system, method and a monitoring device for monitoring air quality of a closed space are disclosed. A plurality of ducts is coupled with the closed space and the plurality of monitoring devices monitors a quality of air inside the plurality of ducts. Each of the plurality of monitoring devices stores a location of placement of each of a monitoring device present inside the closed space, learns a level of carbon dioxide present inside the closed space over a period of time and estimate a number of occupants present inside the closed space based on the level of carbon dioxide present inside the closed space using a machine learning model. Further, the plurality of monitoring devices transmits the monitored quality of air inside the closed space along with the location of the placement of each of the monitoring device and the identified number of occupants to a cloud server.

20 Claims, 17 Drawing Sheets

(56) References Cited

U.S. PATENT DOCUMENTS

2020/0056793 A1\* 2/2020 Etemadi .................. F23N 5/245
2020/0132332 A1\* 4/2020 Mowery .................. F24F 11/59

\* cited by examiner

| @ Regulatory Lookup | ? X |

Exerpt from California Assembly Bill 841 :

(A) Calculation of the required minimum outside air ventilation rates for each occupied area based on the anticipated occupancy and the minimum required ventilation rate per occupant set forth in Table 120.1-A. Calculations shall be based on maximum anticipated classroom or other occupied area occupancy rates and determined by the performing technician. Natural Ventilation shall be designed in accordance with Section 402.2 of the California Mechanical Code (Part 4 (commencing with Section 1.1.0) of Title 24 of the California Code of Regulations) and shall include mechanical ventilation systems designed in accordance with Section 403.0, Section 404.0, or both of those sections, of the California Mechanical Code.

(B) To ensure proper ventilation is maintained throughout the school year, all classrooms shall be equipped with a carbon dioxide monitor that meets all of the following requirements (C) If a demand control ventilation is installed, it shall be adjusted to a carbon dioxide set point of 800 ppm or less and tested by a qualified testing personnel pursuant to Section B of NRCA-MCH-06-A-Demand Control Ventilation Systems Acceptance. If the demand control ventilation system does not maintain average daily maximum carbon dioxide levels below 1,100 ppm, it shall be disabled until such time as the local educational agency determines that the COVID-19 crisis has passed, unless disabling the control would adversely affect operation of the overall system. When disabling a demand control ventilation system, the system must be configured to meet the minimum ventilation rate requirements and tested and adjusted in accordance with paragraph (3) of subdivision (a) of Section 1625. Recommendations for additional maintenance, replacement or upgrades shall be recorded in the assessment report (D) Table 120.1-A states that in a lecture hall for example minimum air rate is 0.15cfm/ft2.

FIG. 20

Air filter Efficiency. The system shall be provided with air filter(s) having a designated efficiency equal to or greater than MERY 13 when tested in accordance with ASHRAE Standard 52.2, or a particle size efficiency rating equal to or greater then 50 percent in the 0.30-1.0 μm range and equal to or greater then 85 percent in the 1.0-3.0 μm range, when tested in accordance with AHRI Standard 680.

D.    Air filter Pressure Drop. All systems shall be provided with air filter(s) that conform to the applicable maximum allowable clean-filter pressure drop specified by i, ii or iii below, when using ASHRAE Standard 52.2, or as rated using AHRI Standard 680, for the applicable design airflow rate(s) for the system air filter(s).

i.    The maximum allowable clean-filter pressure drop determined by the system design for the nominal two inch minimum depth air filter required by Section 120.1(b)1Biia; or ii.    A maximum of 25PA (0.1 in. of water) clean-filter pressure drop shall be allowed for a nominal one-inch depth air filter sized according to Section 120.1(b)1Biib; or

FIG. 22

MACHINE LEARNING MONITORING AIR QUALITY

CROSS-REFERENCE TO RELATED APPLICATIONS

This application claims priority to and expressly incorporates by reference U.S. Provisional Application Ser. No. 63/004,023, entitled "Enhanced HAVC Deployment" dated Apr. 2, 2020 and U.S. Provisional Application Ser. No. 63/074,330, entitled "Air Quality Audit System" dated Sep. 3, 2020, and in their entirety for all purposes.

BACKGROUND

This disclosure relates in general to monitoring quality of air and, but not by way of limitation, to monitoring the quality of air inside a closed space and informing users about a real time status regarding the quality of air.

Quality of air is of rising concern for an individual. Bad air quality may lead to serious health related issues. For example, bad quality of air may cause heart or lungs related issues which may affect the individual over a period of time. To ensure that an individual breathes in fresh air, various air quality monitoring devices have been known in the art.

Various air quality monitoring systems may be installed at various businesses (for example, a restaurant). Since most of the businesses are in a closed space, ensuring a healthy air quality becomes very important. Further, although owner of the businesses may maintain a healthy air quality inside the closed space, this information may not be communicated to customers entering inside the closed space and thus the customers may not know if they would be breathing fresh air once they enter inside the closed space of the business.

Further, for residential spaces, large buildings generally have a heating and ventilation systems which play a critical role in maintaining healthy air quality inside the large building. Since the building is large, a plurality of air monitoring equipment is placed inside the building. Also, the plurality of air monitoring equipment placed inside the building may be placed at a location which may be difficult to access without the intervention of a technician, thereby making difficulty in times of repair of the equipment.

SUMMARY

In an embodiment, the present disclosure provides a system, method and a monitoring device for monitoring air quality of a closed space are disclosed. A plurality of ducts is coupled with the closed space and the plurality of monitoring devices monitors a quality of air inside the plurality of ducts. Each of the plurality of monitoring devices stores a location of placement of each of a monitoring device present inside the closed space, learns a level of carbon dioxide present inside the closed space over a period of time and estimate a number of occupants present inside the closed space based on the level of carbon dioxide present inside the closed space using a machine learning model. Further, the plurality of monitoring devices transmits the monitored quality of air inside the closed space along with the location of the placement of each of the monitoring device and the identified number of occupants to a cloud server.

In one embodiment, the present disclosure provides a system for monitoring air quality of a closed space. The system comprises a plurality of monitoring devices, and a plurality of ducts. The plurality of ducts are coupled with the closed space, and the plurality of monitoring devices are configured to monitor a quality of air inside the plurality of ducts. Further, each of the plurality of monitoring devices stores a location of placement of each of a monitoring device present inside the closed space, and the plurality of monitoring devices are configured to learn a level of carbon dioxide present inside the closed space over a period of time, estimate a number of occupants present inside the closed space based on the level of carbon dioxide present inside the closed space over the period of time using a machine learning model, and transmit the monitored quality of air inside the closed space along with the location of the placement of each of the monitoring device and the identified number of occupants present inside the closed space to a cloud server.

In another embodiment, the present disclosure provides a method for remotely monitoring air quality of a closed space. In one step, a plurality of monitoring devices are provided and a providing a plurality of ducts are provided. The plurality of ducts are coupled with the closed space. The plurality of monitoring devices perform the following steps: monitoring a quality of air inside the plurality of ducts, learning a level of carbon dioxide present inside the closed space over a period of time, estimating a number of occupants present inside the closed space based on a level of carbon dioxide present inside the closed space over the period of time using a machine learning model, transmitting the monitored quality of air inside the closed space along with the location of placement of each of a monitoring device and identified number of occupants present inside the closed space to a cloud server . . . .

In yet another embodiment, the present disclosure provides a non-transitory computer-readable medium having instructions stored thereon, wherein the instructions, when executed by one or more processors of an air quality monitoring system, cause the air quality monitoring system to:

provide a plurality of monitoring devices, provide a plurality of ducts; wherein the plurality of ducts are coupled with the closed space. The plurality of monitoring devices is configured to:

monitor a quality of air inside the plurality of ducts, learn a level of carbon dioxide present inside the closed space over a period of time, estimate a number of occupants present inside the closed space based on a level of carbon dioxide present inside the closed space over the period of time using a machine learning model, and transmit the monitored quality of air inside the closed space along with the location of placement of each of a monitoring device and identified number of occupants present inside the closed space to a cloud server.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures:

FIG. 20 depicts a recent code titled Assembly Bill 841 details operation of ventilation systems in schools;

FIG. 22 depicts an embodiment of a pressing button.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Figure 1:
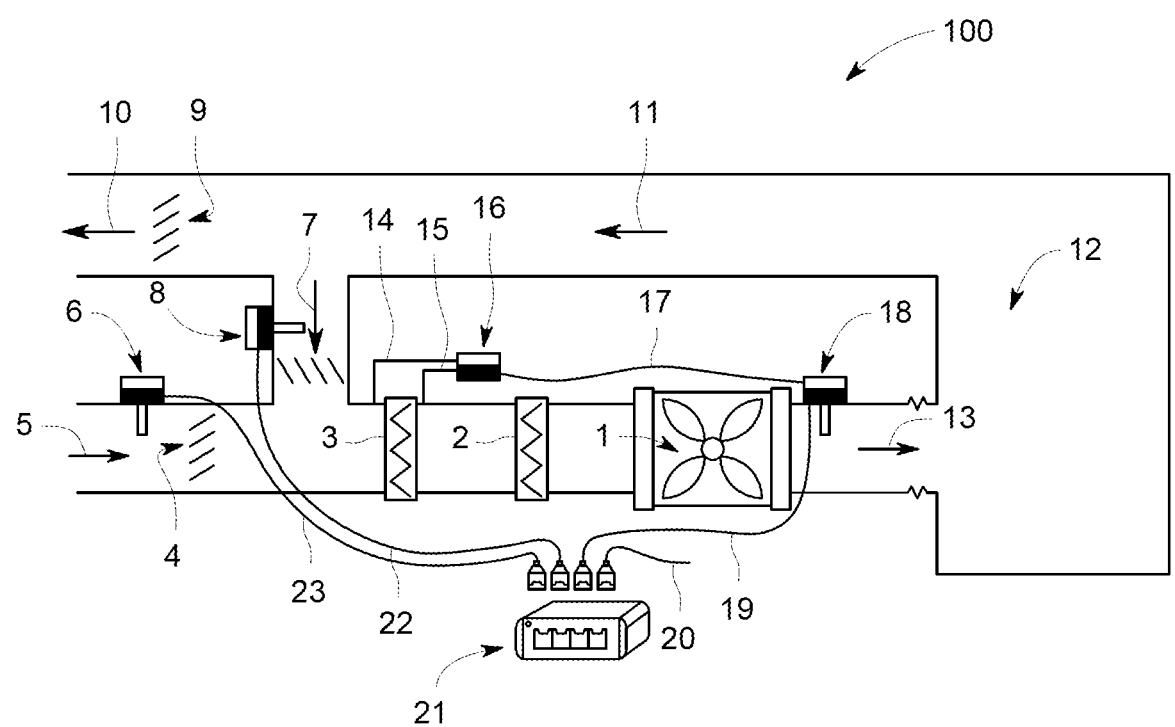
FIG. 1 depicts an embodiment of a system for monitoring air quality in a closed space.

Referring first to FIG. 1, an embodiment of a system 100 for monitoring air quality in a closed space 12 is shown. The system 100 may be present in a plurality of commercial buildings. The system 100 may take air in from outside a building, mix the air with some internal air, expel some air, then may condition the air which may then be distributed around the building. The system 100 includes a main fan 1 which blows the air from the system 100 into the closed space 12. A humidifier 2 and an air filter 3 are shown. A damper 4 moderates the amount of outside air being used. Fresh air is in-taken from an outside air duct 5.

The system 100 comprises a plurality of monitoring devices (6, 8, 16, 18). The plurality of monitoring devices 6, 8, 16, 18 is present inside a plurality of ducts (5, 10, 11, 13) present inside the closed space 12. The plurality of ducts (5, 10, 11, 13) may include one or more passage present in a commercial building for entry or exit of air inside the closed space. The plurality of monitoring devices 6, 8, 16, 18 may be connected using a wire to a cloud server.

The system 100 may comprise of a first monitoring device 6, a second monitoring device 8, a third monitoring device 16 and a fourth monitoring device 18. The first monitoring device 6 may be configured to read or sense the state of the outside air. An air damper 7 controls the amount of air that is being re-cycled from the conditioned air spaces. The second monitoring device 8 may be configured to sense or read the re-cycled air. Yet another louvre or damper 9 controls how much stale air is expelled out of the building. Duct work 10 is used for the extracted stale air. Another ductwork 11 is shown where the used air is returned to the system 100 from the conditioned air spaces. Conditioned air duct 13 feeds air into the conditioned air/occupied space 12. An air tube 14 connects to the dirty side of the air filter 3. Another air tube 15 connects to the filtered air side of the air filter 3. The third monitoring device 16 may be configured to read or sense the differential air pressure across the air filter 3. A first category 5 type cable 17 links the third monitoring device 16 to the fourth monitoring device 18 which may be configured to read or sense the quality of the conditioned air being fed into the conditioned air/closed space 12. A second category type 5 cable 19 connects the fourth monitoring device 18 to a Power over Ethernet (POE) switch 21. The POE switch 21 provides data connection and 48 VDC power to the fourth monitoring device 18. A third category 5 type cable 20 links the POE switch 21 to an IT network of the building and a connection to the Internet. A fourth category 5 type cable 22 provides data and power to the second monitoring device 8 for reading the return/re-cycled air. A fifth category 5 type cable 23 provides data and power to the first monitoring device 6 which is reads the quality of the incoming fresh air.

Figure 2:
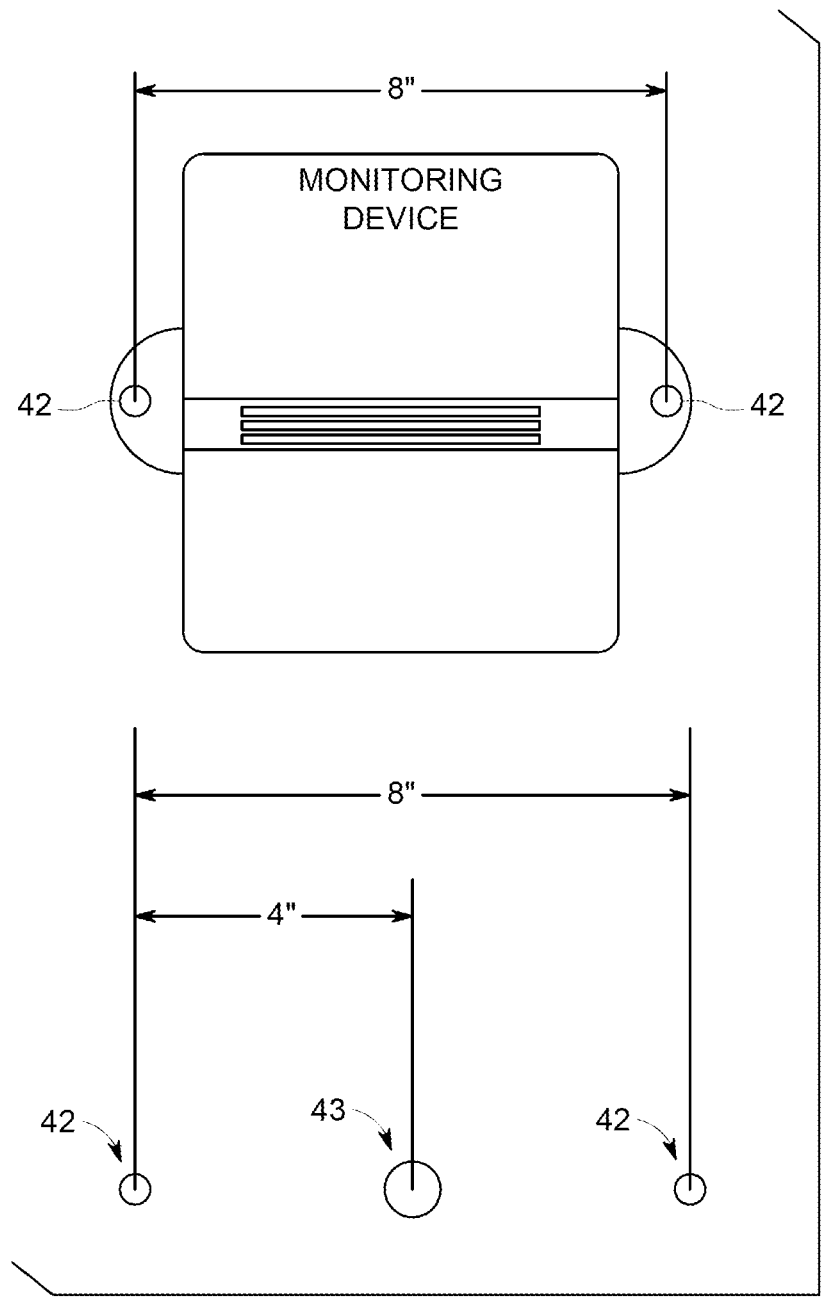
FIG. 2 depicts an embodiment of a plurality of monitoring devices coupled to a plurality of ducts inside a closed space.

Referring next to FIG. 2, an embodiment of the plurality of monitoring devices 6, 8, 16, 18 coupled to the plurality of ducts (5, 10, 11, 13) inside the closed space 12 is shown. A one-half inch hole 43 may be drilled at one side of a duct to accept the sensor portion of the monitoring device. Two self-tapping holes 42 may be used to securely fix the monitoring device to the side of the duct. Although one monitoring device has been shown in the figure fixed to the duct, similar arrangement may be applicable for other monitoring devices as well.

Figure 3:
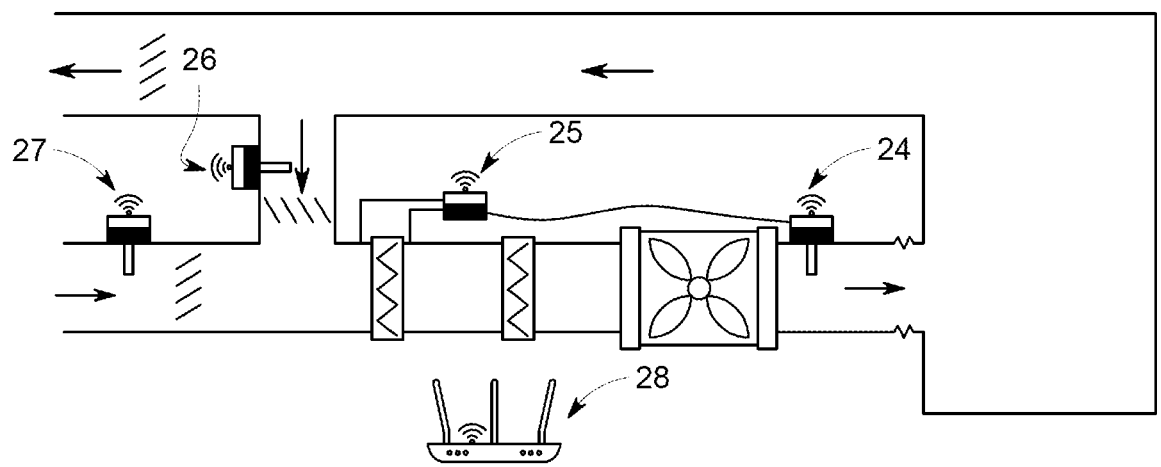
FIG. 3 depicts an embodiment of a plurality of monitoring devices communicating wirelessly.

Referring next to FIG. 3, an embodiment of the plurality of monitoring devices 6, 8, 16, 18 communicating wirelessly is shown. The wireless communication may be established by connecting the plurality of monitoring devices 6, 8, 16, 18 to the Internet using Wi-Fi. Wireless installation can sometimes be simpler for retrofit applications whereas installing wires can be time consuming. The plurality of monitoring devices 6, 8, 16, 18 are installed using Wi-Fi. Each of the monitoring devices 6, 8, 16, 18 may include a Wi-Fi transmitter (24, 25, 26, 27). The Wi-Fi transmitters (24, 25, 26, 27) present in each of the monitoring device may communicate to a building Wi-Fi shown by a wireless access point 28.

In one embodiment, some buildings may have air conditioned using a fan coil. The fan coil operates in a similar manner as that of the system 100 but does not bring in fresh air from the outside and only recycles the air in the room. This sort of installation is prevalent in smaller spaces such as hotel rooms, hair salons and homes.

Figure 4:
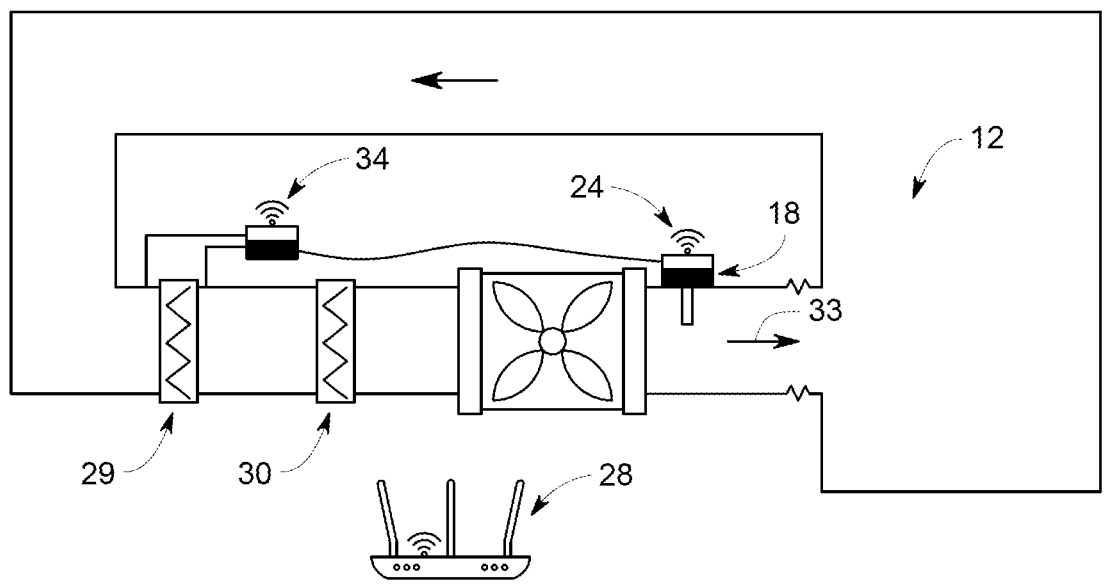
FIG. 4 depicts an embodiment of a typical installation of a system with a fancoil device.

Referring to FIG. 4, an embodiment of a typical installation of the system 100 with a fancoil device is shown. The fourth monitoring device 18 reads or senses the conditioned air being supplied to the closed space 12 using the first Wi-Fi connection 24. The wireless access point 28 may connect the plurality of monitoring devices 6, 8, 16, 18 to the internet. An air filter 29 and an optional humidifier 30 are shown. The third monitoring device 16 reads or senses the status of the air filter 29 using a fifth Wi-Fi connection 34. A conditioned air duct 33 provides conditioned air duct supply to the closed space 12. The wireless access point 28 connects the plurality of monitoring devices 6, 8, 16, 18 to a central system which is used to connect the plurality of monitoring devices 6, 8, 16, 18 to the internet.

Figure 5:
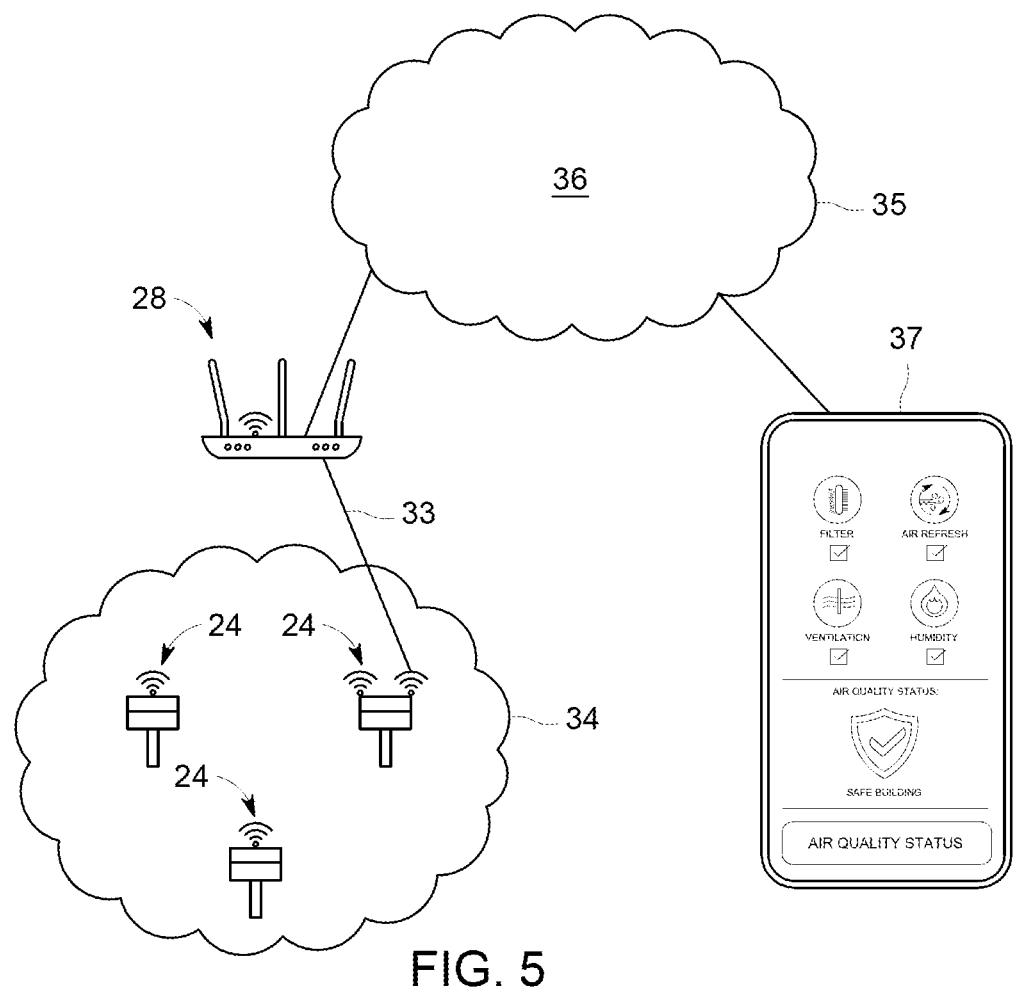
FIG. 5 depicts an embodiment of a schematic of how data is transmitted in a system.

Referring to FIG. 5, an embodiment of a schematic of how data is transmitted in the system 100 is shown. The system 100 comprises the plurality of monitoring devices 6, 8, 16, 18 6, 8, 16, 18 that may use their built in Wi-Fi connection 24 to communicate with each other by creating a mesh Wi-Fi network 34. This network 34 may use mesh Wi-Fi standard 802.11s. One device in the mesh Wi-Fi network 34 may be nominated based on the best signal strength and may connect to the wireless access point 28 using the device's second built in Wi-Fi controller 33. This second Wi-Fi controller 33 may use standard 802.11n which is available on most Wi-Fi access points. The Wireless access point 28 may connect to the Internet 35.

A cloud server 36 for example, Amazon Web Services (AWS) or Microsoft Azure is shown. The cloud server 36 may store the air quality data transmitted from the monitoring devices and may make it access to the users.

If the connection to the Wi-Fi access point 28 fails, the mesh network 34 may automatically appoint another device to connect the mesh Wi-Fi network 34 to the Wi-Fi access point 28.

The mesh network 34 may be given the login credentials to two separate Wi-Fi access points. This may provide plurality of monitoring devices 6, 8, 16, 18 with a backup method to store data to a data store of the cloud server 36.

The system 100 may gather information about various areas of a building. This information may be stored in the cloud server 36. Artificial Intelligence (AI) algorithms may be used to analyze the data. These AI algorithms may compare the data to a plurality of templates to predict and learn occupancy inside the closed space to provide an owner of the closed space/businesses with information indicating compliance of the building with industry standards.

The information thus collected from the closed space 12 is shown to a user in a mobile application. The mobile application may be used by the occupants, owners and clients of the spaces to view and interact with the plurality of monitoring devices 6, 8, 16, 18.

Figure 6:
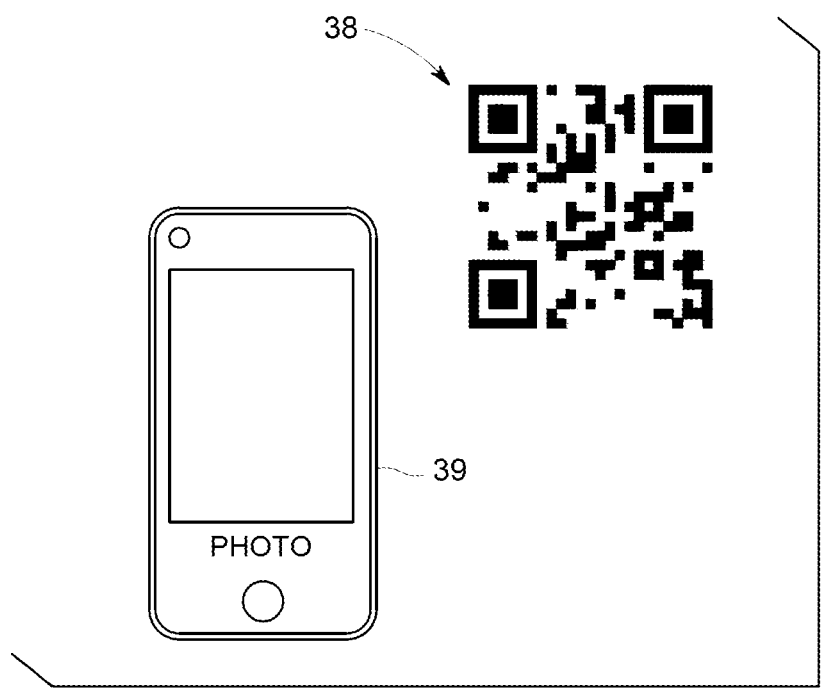
FIG. 6 depicts an embodiment of a technique for viewing an information collected from a closed space.

Referring to FIG. 6, an embodiment of a technique for viewing the information collected from the closed space 12 is shown. A poster or label 38 may be attached outside or within the closed space 12. The poster or label 38 may contain a dedicated QR code. A computing device 39 with a camera, scans the dedicated QR code 38 to obtain a view of the air quality on the mobile application running on the computing device 39.

Figure 7:
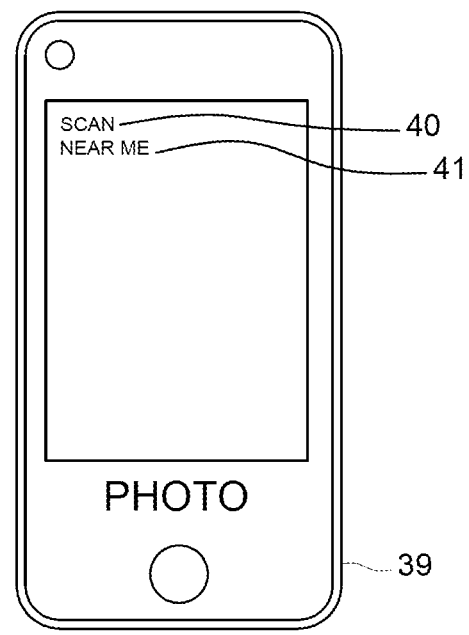
FIG. 7 depicts an embodiment of an operation of a mobile application running on a computing device.

Referring next to FIG. 7, an embodiment of an operation of a mobile application running on the computing device 39. A user of the mobile application may select a scan option 40 to scan the QR code 38. Upon scanning the QR code 38, the user may be displayed with a plurality of options to view the air quality at various locations. The user may select "NEAR ME" option 41 if the user wants to look for buildings, or businesses nearby that have plurality of monitoring devices installed using Global Positioning System (GPS).

Figure 8:
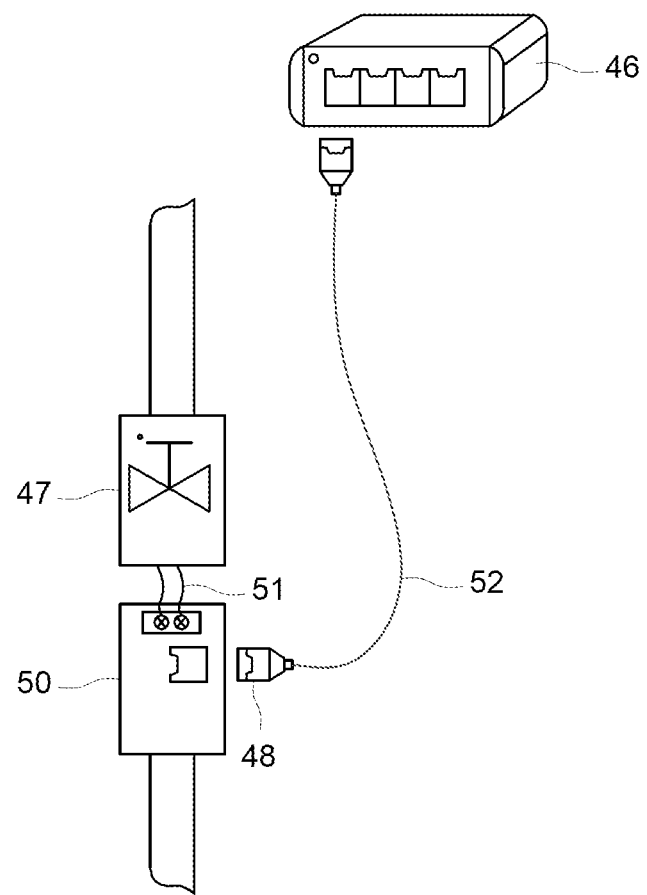
FIG. 8 depicts an embodiment of an installation of a plurality of monitoring devices.

Referring next to FIG. 8, an embodiment of an installation of a plurality of monitoring devices 6, 8, 16, 18 is shown. Generally, devices for heating, cooling and ventilation such as zone valves and air dampers installed inside the buildings require 24 VAC power to operate. Traditional installations require a local 24 VAC transformer to be installed. Each of the monitoring device may provide a simpler installation by providing power and communication using a single category 5 type cable. Zone valves, zone dampers 47 and other external devices may connect to a monitoring device from the plurality of monitoring devices 6, 8, 16, 18 to a controller 50. The monitoring device may then connect to the Ethernet data router or switch 46 with Power over Ethernet (POE) via a single CAT5 cable 52.

The POE Ethernet router/switch 46 may insert the 48 VDC onto the communication wires in the CAT5 Ethernet cable.

The POE Ethernet router/switch 46 may turn on/off the power to each cable via a console or an Application Programming Interface (API), so this may allow a distributed device located somewhere in the building to be power cycled from anywhere potentially saving an engineer from having to gain access to an external device 47.

The CAT5 cable 52 may terminate to a conventional RJ45 jack 48 which plugged into the monitoring device. The dominance of the IT market has meant there are plethora of trained professionals who can terminate CAT5 cables very cost effectively and reliably. Alternatively, conventional installations require termination of RS485 networks using twisted pair such that this installation method is more prone to error and failure and is much less common than IT networks. It means the installation process requires more specialization and training to be reliable. So CAT5 cable installation of this embodiment reduces installation cost over conventional installations.

The jack plugs into the monitoring device, that generally mounts very close to an external device so the external device leads 51 (generally ½ meter or less) can terminated straight into the monitoring device. This saves a cable termination for installation which again improves reliability and decreases installation time.

Figure 9:
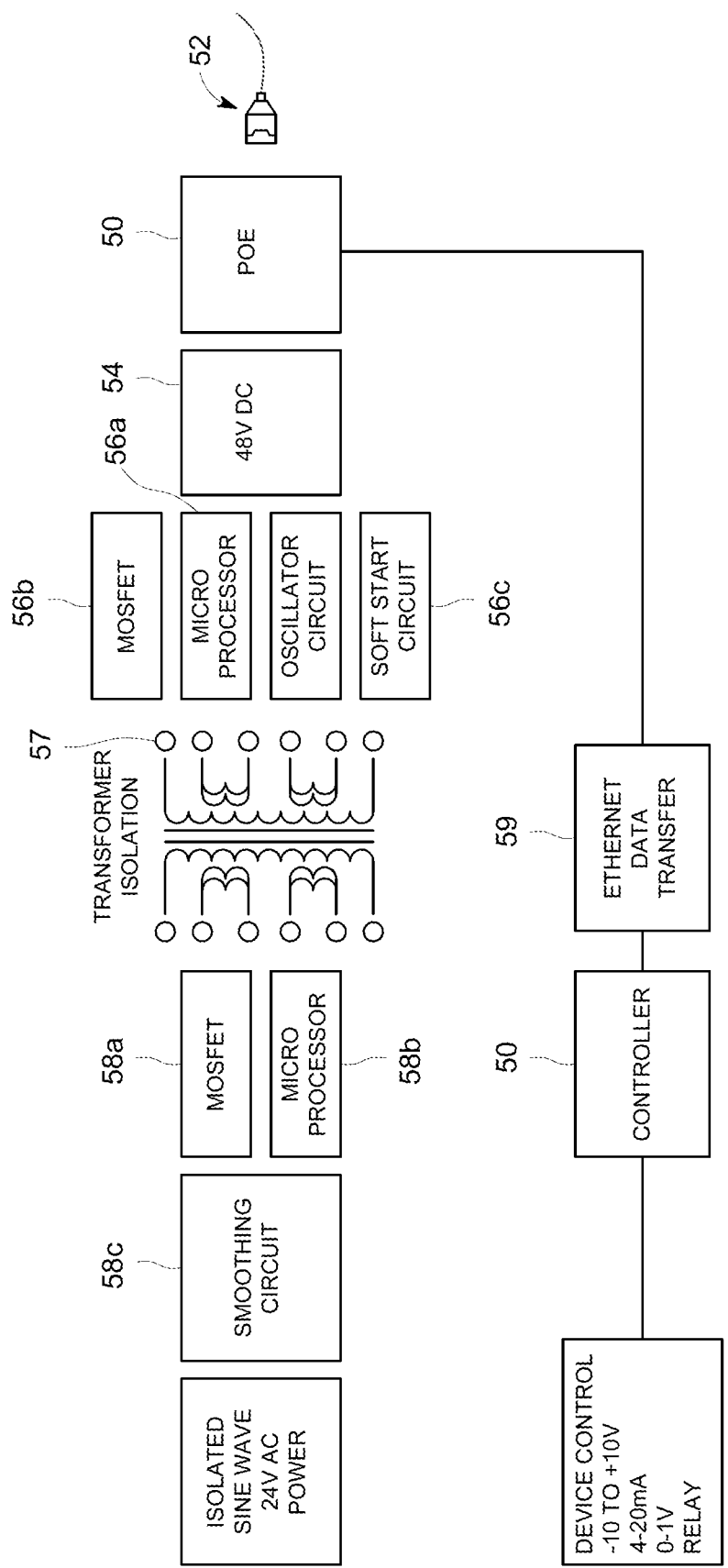
FIG. 9 depicts an embodiment of a power circuit required to convert POE (48 VDC) into 24 VAC to power an external device.

Referring next to FIG. 9, an embodiment of a power circuit required to convert POE (48 VDC) into 24 VAC to power the external device 47 is shown. The plurality of monitoring devices 6, 8, 16, 18 may comprise a power controller. Inside the monitoring device controller 50, ethernet data signals are split from the power signals and may be isolated via a transformer 59 and then may be connected to a microprocessor 56a. This provides high speed Ethernet communications.

The POE power signals may be supplied via two sources compliant with the POE standards 802.3AF and 902.3AT. These signals are each fed into a diode bridge to correct for polarity then fed into a power converter 56.

A POE circuit 54 may negotiate with the POE Ethernet switch 46 using a predefined cable impedance test so that the POE Ethernet switch 46 can power on to the circuit. This results in a 48 VDC power supply up to 25 watts. This negotiation process also ensures that if there is too much power drawing from the POE circuit 54, the power is turned off by the POE Ethernet switch 46 and the equipment remains safe.

This 48 VDC signal may then generate a low voltage supply which powers the microprocessor 56a. The microprocessor 56a may monitor the input voltage and may wait until a suitable voltage (for example, greater than 38V) is available and may start the oscillation. Two power Mosfets 56b may drive two primary windings on transformer 57 and may feature a soft start circuit 56c to reduce inrush as the transformer magnetic field is powered. A third set of windings may distribute power to an isolated-side microprocessor. An isolated-side microprocessor 58b may monitor for over voltage supply and may power the circuit down if the input voltage becomes too large (for example, greater than 54 VDC).

An additional Mosfet 58a may be added to the circuit. This is so that when the power stops, the high voltages stored in the magnetic transformer 57 are not released back onto cable 52.

On the isolated side of the transformer, the microprocessor 58b may monitor the voltage generated by the main switching Mosfets. The Mosfets creates three DC power rails. 0, 60 and 120 VDC. The secondary mosfets 58a may switch these voltages to generate a square wave using the middle DC 60V rail as ground. This square wave is fed to an inductor capacitor network 58 to provide a smooth and isolated 24 VAC sinusoidal output which may then use to power one or more external devices.

The POE standard may specify that any external device or connections to external devices may be electrically isolated from the POE Ethernet switch 46. This may be achieved by driving an oscillating 48 VDC signal into an isolating transformer and recreating an isolated 24 VAC power supply on the secondary side of the transformer. Data may also be isolated using a transformer built into the RJ45 jack ensuring compliance.

Figure 10:
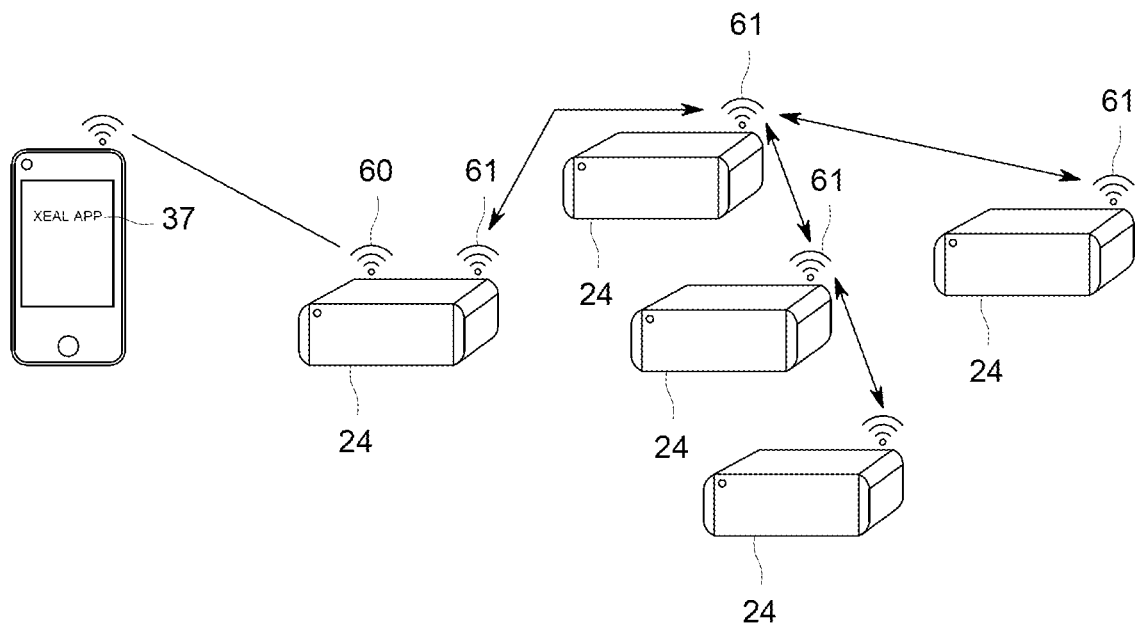
FIG. 10 depicts an embodiment of a plurality of monitoring devices 6, 8, 16, 18 installed in a closed space.

Referring next to FIG. 10, an embodiment of a plurality of monitoring devices 6, 8, 16, 18 installed in a closed space 12 are shown. Each of these devices 6, 8, 16, 18 may send air quality data to the cloud server 36. Each device may have credentials to access the Wi-Fi. Each device may know in which building it is installed and may be able to communicate with both a cloud database and separately with a user. Supplying this information for each device in a building network is known as commissioning.

In one embodiment, the plurality of monitoring devices 6, 8, 16, 18 may operate as a peer-to-peer networking devices so there is no central controller or a central database of the devices.

The commissioning process may be a combination of electronic hardware and software that may allow a single button press on the mobile application running on a computing device to connect with a computing device. Through this computing device user's contact information, especially email details, is distributed to all devices running in the building ensuring that each monitoring device is configured to monitor itself and can contact the user if it is in need of service and can start sending air data to the cloud server 36.

Figure 11:
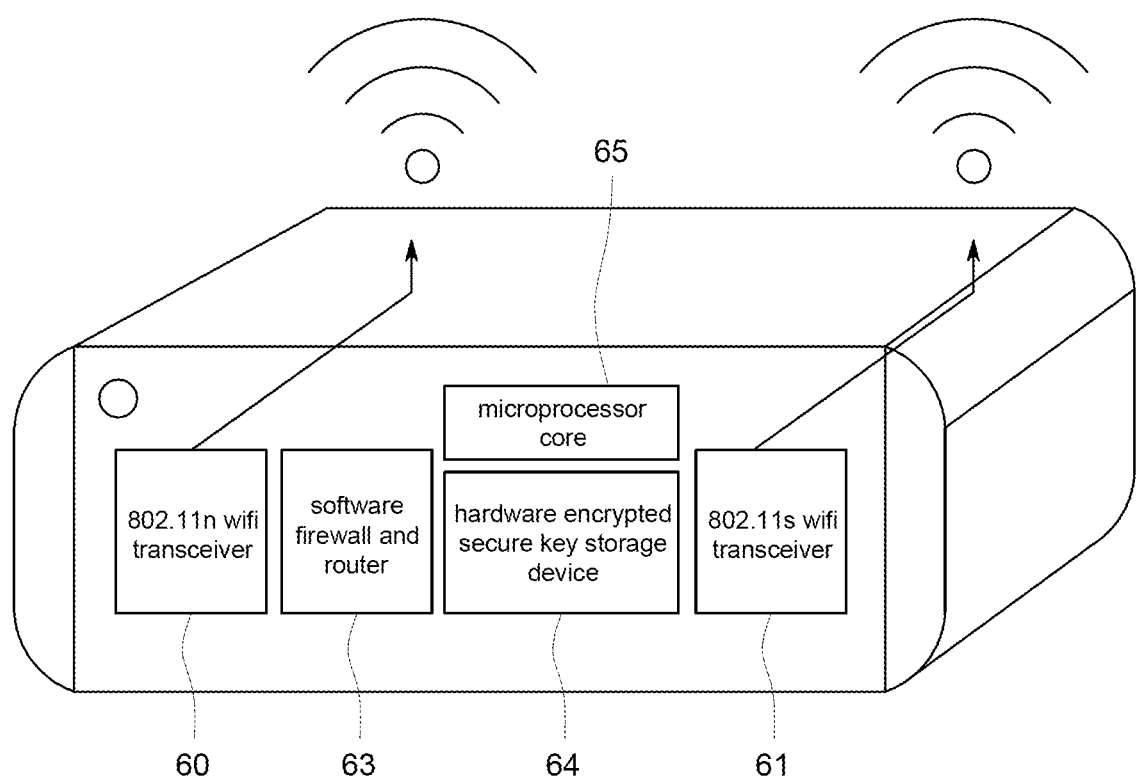
FIG. 11 depicts an embodiment of a block diagram of a monitoring device from a plurality of monitoring devices.

Referring next to FIG. 11, an embodiment of a block diagram of a monitoring device from the plurality of monitoring devices 6, 8, 16, 18 is shown. Each device may be fitted with two Wi-Fi modules 60, 61. One Wi-Fi module 60 may be used for public access (802.11.n) and the other 61 for private and secure mesh networking (802.11s). Other embodiments could use any type of radio communication for the mesh networking including Bluetooth™, ZIGBEE™, etc.

The two Wi-Fi modules 60, 61 may be isolated by a software router/firewall 63 controlled by a microprocessor 65. Information may propagate seamlessly from mesh to public Internet, but the public Internet may have restricted access to the Wi-Fi mesh.

Each monitoring device upon powering up, may broadcast a discovery message on the secure mesh network 61. Each monitoring device may use Universal Plug and Play (UPnP) protocol, but other discovery protocols may also be used. If the monitoring device is within range, the two monitoring devices mutually authenticate each other using their integrated secure crypto hardware chip 64. The hardware chip 64 is a tamper proof device containing a secure digital key for each device microprocessor 65. This secure digital key 64 may allow the monitoring device to network with other monitoring devices in a trusted network. With this trust, all monitoring devices 6, 8, 16, 18 may power up and may join the mesh network 61. The mesh creation happens without human intervention. The mesh network 61 may provide a secure communications network for all the monitoring devices 6, 8, 16, 18 forming a robust control network.

Many of the monitoring devices on the secure mesh network 61 operate without manual configuration so they can discover their required partner devices and start to operate automatically. For example, a fan can discover all the "end stop" demand signals in all the thermostats and can use this signal to start or stop without an installer having to program this low-level functionality.

Each of the devices may have a pubic Service Set Identifier (SSID) generated by Wi-fi controller 60. To optimize building bandwidth, it may be useful to minimize the number of SSID devices broadcasting. For a monitoring device which may have recently joined the mesh network 61 can "see" this default SSID being broadcast from another monitoring devices connected to the mesh network 61. So, the newly joined monitoring device may not activate its own public Wi-Fi connection. Depending on the geography of the installation it is possible that more than one monitoring device may broadcast the default SSID Wi-Fi. Now all monitoring devices 6, 8, 16, 18 may communicate with each other using the mesh wifi system and at least one monitoring device may be configured as a wireless access point allowing connection to computing devices.

Once the plurality of monitoring devices 6, 8, 16, 18 has been powered up and installed, the user may want to check if all the monitoring devices 6, 8, 16, 18 are operating correctly.

Figure 12:
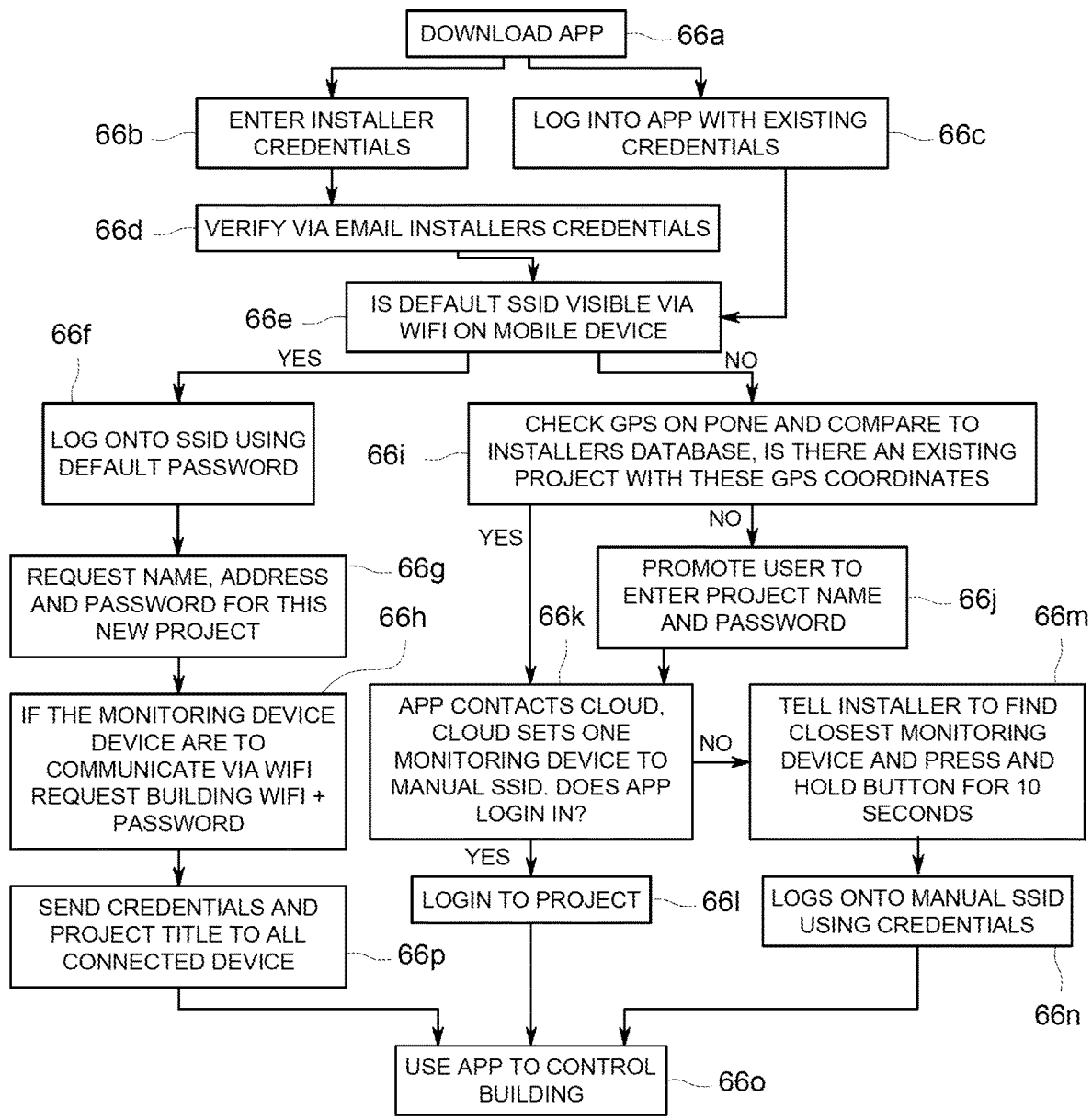
FIG. 12 depicts a flow chart of a process for checking if all the monitoring devices are operating correctly.

Referring next to FIG. 12, a flow chart of a process for checking if all the monitoring devices 6, 8, 16, 18 are operating correctly is described. A user first downloads the mobile application onto their computing device 66a. When they first open the mobile application 37, the mobile application 37 prompts the user for their email details and verifies the user. If the mobile application has already been used the user, the user may log in 66c. However, if the user has never used the mobile application before, the mobile application prompts the user to enter the credentials 66b and then verify the email address 66d.

When the user has been verified, the mobile application 37 may search for a default Wi-Fi SSID used by the monitoring device on the built in Wi-Fi controllers 66e. If this default SSID is present, the mobile application 37 may connect to the default SSID automatically without the need to prompt the user for login credentials 66f.

For many applications, all the users may want to give their credentials to each monitoring device 6, 8, 16, 18 so that the monitoring devices 6, 8, 16, 18 may communicate their maintenance status. A button called "Commission All" may be pressed on the mobile application 37. If this project was previously un-commissioned, a prompt to enter a Project Name, address and a password appears 66g.

The plurality of monitoring devices 6, 8, 16, 18, if they are not connected via POE, may need to login to the buildings Wireless Access Point. The mobile application 37 may prompt the user for the building Wi-Fi SSID and the password 66h.

The mobile application 37 may then connect the computing device 39 to a monitoring device which is currently acting as a Wireless Access Point with a default name and password.

The mobile application 37 may access the current location signals from the user's computing device 39 and may store this data to all the installed monitoring devices 6, 8, 16, 18. It may allow for tracking of monitoring device and other useful data and may provide the location of the monitoring device for users using the mobile application 37.

When the user has completed his work, the user may leave the mobile application 37. At this point the mobile application 37 may disconnect from the wireless access point of the monitoring device. The mobile application 37 may then communicate with a monitoring device network to use the security credentials to secure the network and re-boot. Upon re-boot, the monitoring device will no longer broadcast its default SSID, but may log into the building's Wi-Fi network so devices can communicate to the cloud server 36.

This embodiment may allow a one click process to communicate credentials to plurality monitoring devices 6, 8, 16, 18 on a secure mesh network 61 without the need to access monitoring devices 6, 8, 16, 18 physically or individually.

Once commissioned, if a monitoring device is missing some configuration data or is not functioning correctly, both immediately and in the future, the monitoring device may notify the user with its maintenance requests and the user may address the maintenance request of the monitoring device.

In one embodiment, if the mobile application 37 does not find a default SSID Wi-Fi hotspot broadcast by the monitoring device 66e, this generally may mean that the system 100 has already been commissioned and so has its own network and secure passwords. The mobile application 37 may check the user's database in the cloud for installations that match the location of the computing device. If not available, the mobile application 37 may request login information from the installer.

With the login details, the mobile application 37 may now attempt to connect to the monitoring devices 6, 8, 16, 18. The normal method is for the mobile application 37 to log into the building's Wi-Fi network and may connect to monitoring devices.

If there is an issue with the local Wi-Fi network, the mobile application 37 may connect to the cloud server 36 and may send a message to the monitoring device to re-establish the default (manual) SSID so the computing device may communicate directly with the monitoring device without the building's Wi-fi network.

If the cloud server 36 is not able to make this connection, the user may reach the monitoring device and push and hold the reset button for 10 seconds. This forces the monitoring device to re-establish the default (manual) SSID wireless access point so the computing device may connect to this monitoring device. As soon as it has connected to this local device, it can communicate with all monitoring devices via the mesh Wi-Fi network. The user may use a project password as for security reasons the monitoring device used to begin the installation is no longer valid.

The system 100 is designed to inform a building owner of how the system 100 in their building is performing and to inform the users of the space on the health of the workplace. The system 100 may have levels of access of data for different category of users. For example, the building owner may want to provide some staff with sufficient information while providing others with detailed information on the air quality of the building.

Figure 13:
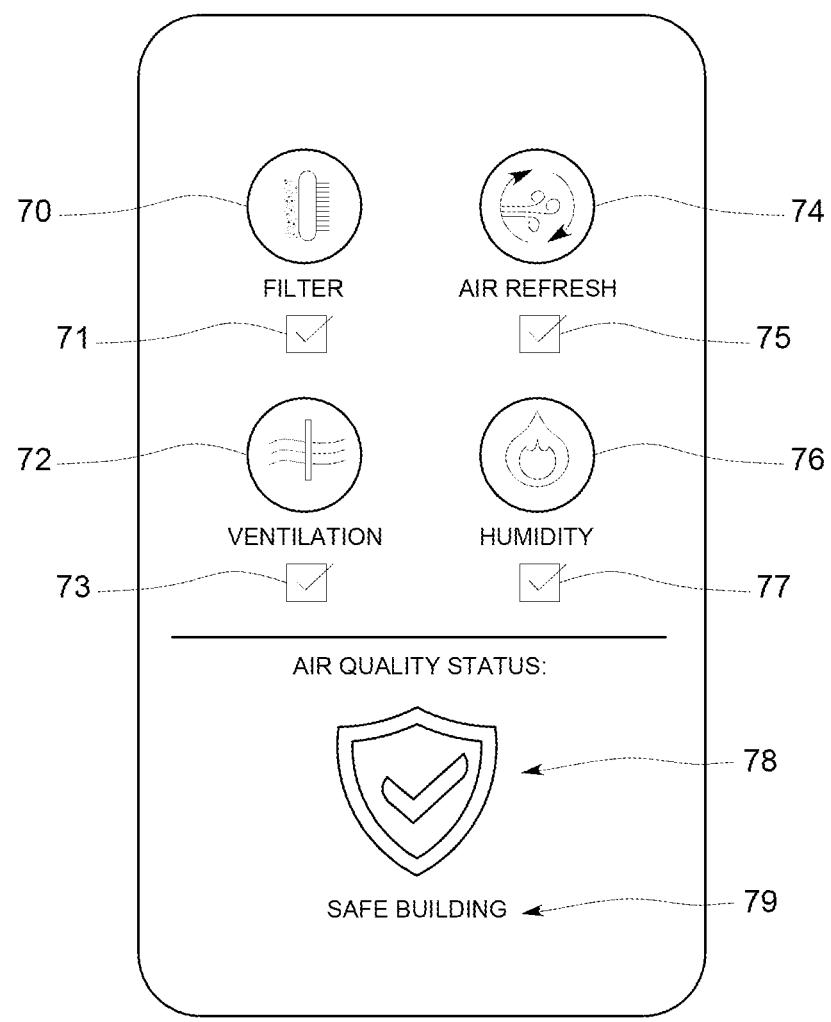
FIG. 13 depicts an embodiment of a lowest level of access for the mobile application.

Referring next to FIG. 13, an embodiment of a lowest level of access for the mobile application is shown that may represent a summary of all the collected information about air quality.

For a space to be healthy, the plurality of monitoring devices requires a filter. The status of the filter is represented by 70. The monitoring device may detect a differential pressure sensor on either side of the filter to determine the type of filter and the cleanliness of the filter. Air filters may be categorized by their filtering ability from MERV1 to MERV20. A dirty filter does not sacrifice cleanliness just fan efficiency. A casual user of the mobile application may be concerned about the MERV rating of the filter, not especially about when it was last changed. A graduated scale may be used with traffic light Red/Amber/Green check marks 71 to indicate the rating of the installed filter.

Figure 14:
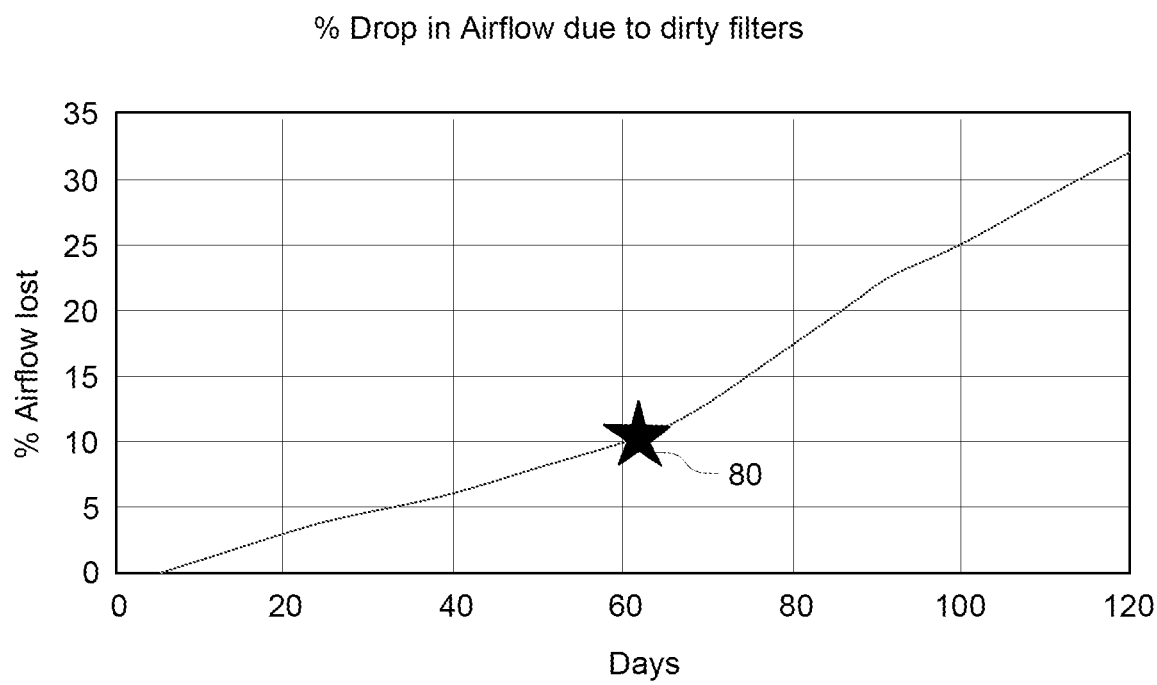
FIGS. 14-17 depict graphs in accordance with an embodiment of the present invention.

A building manager may have permissions such that pressing the icon 70 on the mobile application would open a secondary window shown in FIG. 14. The graph shown in FIG. 14 shows the user for how long the filter has been installed 80, and how much efficiency the system has lost owing to dirt on the filter. Some suggestions as to when the filter should be changed may also be indicated and the system 100 may automatically send out text messages to the user when the filter should be changed.

Another characteristic of a healthy space is how often the air is changed, 72. A good guideline for a healthy workplace would be a minimum of 8 air changes per hour during occupancy. A traffic light colored check mark, 73 is used to indicate this metric.

Figure 15:
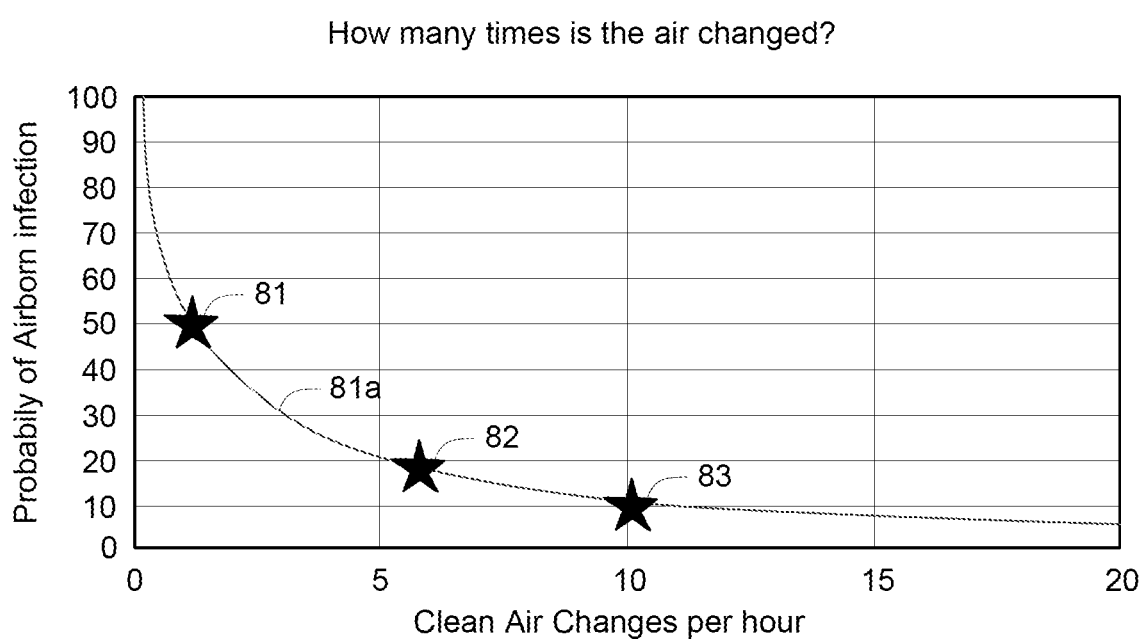

A click on this icon 72 may provide further information as shown in FIG. 15. The graph shown in FIG. 15 shows the likelihood of catching an airborne virus or pathogen versus the number of times the air has been exchanged and filtered. A star 81 in the graph of FIG. 15 may indicate where the system stands in real time. The star 81 may move up and down the curve 81a based on the status of the system such as fan speed. The algorithm works out a traffic light color code for the star as it moves along the graph so an unhealthy space will show the star 81 in red as there is less than 1 air changes per hour, a healthy space would show a green star 83 with air changes greater than 8 time per hour. The spaces before will be indicated in yellow, 82.

The health of the air may also be dependent on the amount of outside air that is used as shown by icon 74. To balance energy use, the amount of outside air used may be changed on an ongoing basis with less being used during the nighttime periods than during occupied times. The carbon dioxide ($CO_2$) level may also be considered as if the $CO_2$ readings get high, more outside air is required for healthy spaces. A traffic light approach may also be taken here to indicate the health state. The summarized data may be intentional as institutions have discovered a fascination among occupants of spaces to specific metrics such as the $CO_2$ reading in ppm which may be time consuming due to lack of knowledge of the overall health of the space.

Figure 16:
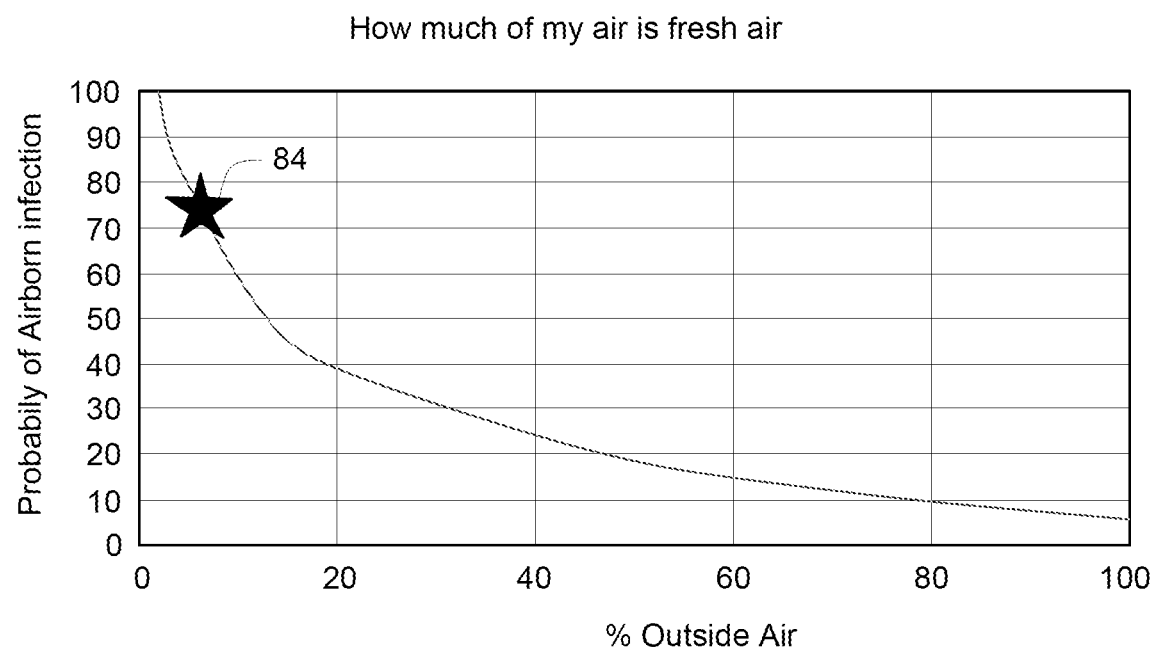

Clicking on icon 74 will display a graph shown in FIG. 16 subject to the user's permissions. The current state of the closed space with regards to outside air is shown by 84. The current state of the air highlighted by the location of the star 84 shows only 5% of outside air is being used which causes a risk of 70% of catching an airborne pathogen.

Figure 17:
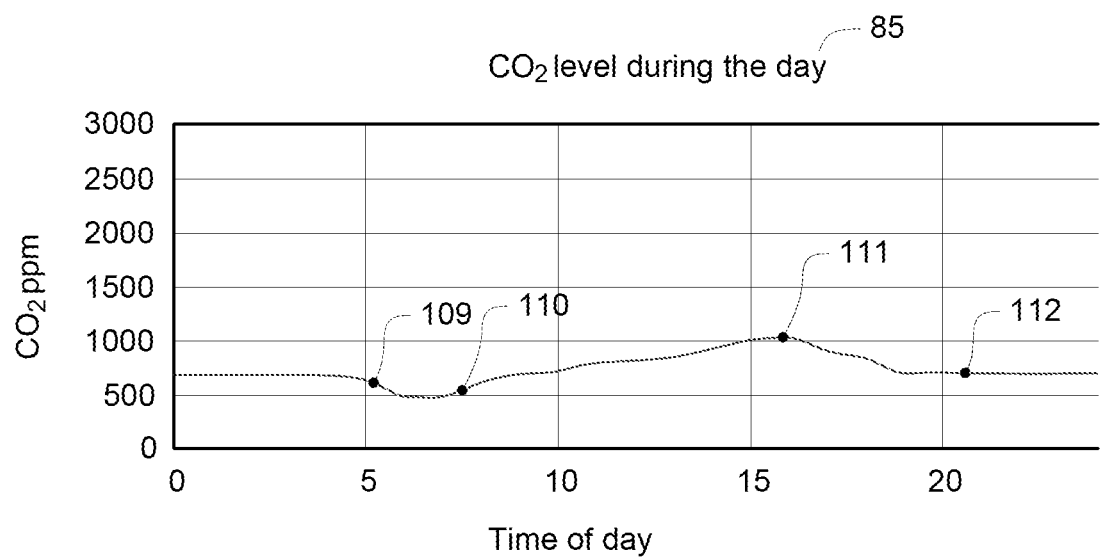

FIG. 17 is also available for showing the $CO_2$ levels in real time shown by 85. This graph shown in FIG. 17 shows that the space becomes occupied around 7 am 110. Building codes require that 2 hours before a space is occupied, the air is actively changed in the space. To change the air in a closed space, the control system turns up the fan speed 1 and opens the outside air damper 4 which results in a drop in $CO_2$ levels 109.

In one embodiment, the closed space 12 may fill up with people and the $CO_2$ levels start to climb despite the operations of the fan to change the air. At around 3.30 pm, the closed space may start to empty 111. Building codes may require that the air system continues to flush the air until 1 hour after occupancy. This is shown by a drop in the $CO_2$ level until the fan stops shown by 112. At this point, the fan may not be operating, the space may not be occupied so the $CO_2$ levels stay approximately the same until the cycle starts the next day. With knowledge of this, a pattern may be sensed in the learning AI algorithm to understand occupancy.

An overall summary of all building data may be shown in FIG. 13 by the check mark 79. This check mark may also be color coded with red/yellow/green for simple understanding on the health state of the building. This check mark may be the sum of all the tests performed by artificial intelligence models to determine if the building is compliant with current building codes and mandates.

The monitoring devices 6, 8, 16, 18 in networked systems may be able to communicate with one another. The monitoring devices 6, 8, 16, 18 may require a digital address for example, an Internet Protocol address (or similar solution for Zigbee or BLE mesh networks to be unique on a network. To share data with other monitoring devices 6, 8, 16, 18 or communicate with a secure cloud server 36, the monitoring devices 6, 8, 16, 18 must have security credentials. This information is provided during the installation process. Once configured during the installation process, a monitoring device becomes unique. This unique nature poses a maintenance problem should that if the monitoring device fails, mere replacement with another blank monitoring device is an issue. Traditionally, service engineers would connect to a network using a laptop or computing device available with them and do a manual "replace device" requiring a database of networked data and devices. This requires some skill and training and a copy of the network database.

Figure 18:
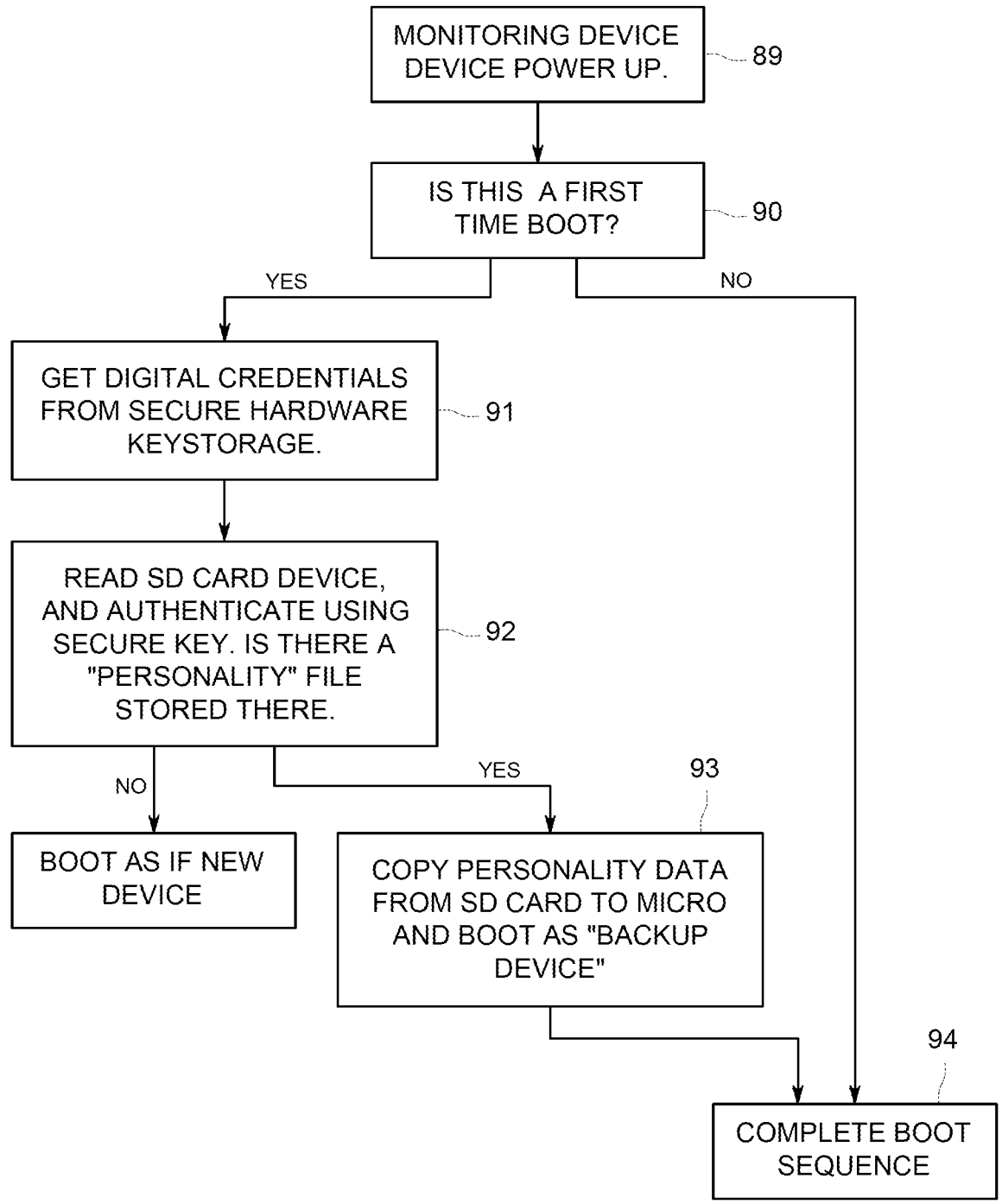
FIG. 18 depicts a flowchart of a method to replace a unique device without the need for any network skills nor access to an APP.

Referring next to FIG. 18, a flowchart of a method to replace a unique device without the need for any network skills nor access to the APP is shown.

The monitoring device powers up 89 and checks its memory to see if it has been configured before 90. Each monitoring device 6, 8, 16, 18 is equipped with an secure digital (SD) card memory device. The SD card memory device may be used as a backup for historical sensor data and may hold a copy of the device's "unique personality". This "unique personality" contains Internet Protocol (IP) address and other unique details about the monitoring device such as a unique location used by the cloud server to uniquely identify data relating to monitoring device. If the monitoring device senses that previous configuration has, the monitoring device may access a secure digital key stored on a tamper resistant silicon part on a printed circuit board 91 present in the monitoring device. This key may then be used to decrypt the personality file stored in the SD card 92. This personality file may be used to configure new monitoring device 93. This means that to replace a faulty monitoring device, the SD card from the old monitoring device may be inserted into the new monitoring device and the new monitoring device boots and assumes the old device's personality without further interaction 94.

In one embodiment, networked systems generally use unique identifiers called media access control (MAC) addresses. These are often hard coded into silicon part and so will change if the monitoring device is replaced. To ensure continuity of data in the cloud server 36, the monitoring device may generate a randomized unique location string. This unique location string may be used as the identifier for data being stored to the cloud server 36 and may be stored in the personality profile. This ensures migration to a replacement monitoring device, if needed.

In one embodiment, once the monitoring device has been successfully booted and acquired an address, the monitoring device can then publish itself to the cloud server 36 through the network. This informs other monitoring devices about the monitoring device.

In one embodiment, a thermostat may find a fan, and may try turning on this fan to see if the temperature it is sensing changes. A zone valve might find a pump and could turn the pump on and detect if it is connected. Using a trial and error, the monitoring devices 6, 8, 16, 18 can automatically start to build their own dependencies hugely reducing the time it takes to commission a building.

When working with data, it is important to ensure all data points are within reasonable boundaries. Failure to do so can destabilize an Artificial Intelligence algorithm. If a sensor in the monitoring device reports a temperature of 200 F for outside air, this value is clearly not valid and should be discarded.

Figure 19:
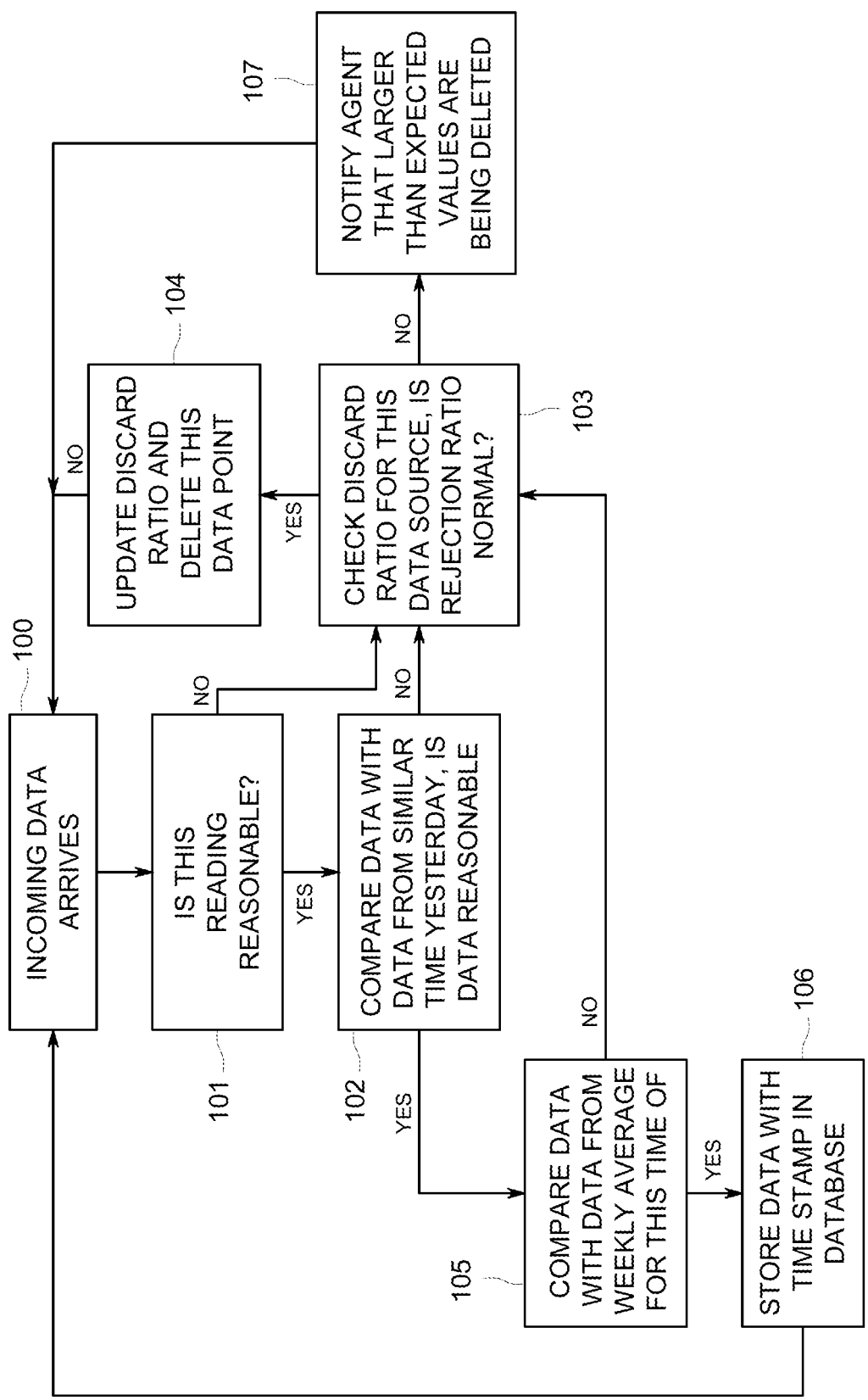
FIG. 19 depicts a flow chart of a process of comparing a temperature of outside air with a predefined value.

Referring next to FIG. 19, a flowchart of a process of comparing a temperature of outside air with a predefined value is shown. Data is received from a monitoring device with a time and date stamp and a unique location code generated by the monitoring device 110. There are some basic rules for each data type to get the system started with reasonable data. An example of such a rule would be "the limits for reasonable air temperature are 50 F to 150 F. Any values outside these numbers are discarded shown in 101. This starts the learning routine with reasonable boundary cases.

In one embodiment, it may be possible to look at historical data, same time yesterday to further fine tune data for abnormalities shown in 102.

The historical weekly average for current time of year may then be compared to historical time and data to further fine tune data for abnormalities shown in 105.

Only when data has been assessed to be reasonable, it may be stored along with the time and date stamp 106.

In one embodiment, a data point may be corrupted. This can be a one-off case and the data is just ignored 104. If lots of data points begin to be outside boundary conditions, this may indicate that either the sensor or some aspect of the monitoring device may be faulty. A count of the number of datapoint deletions per period, called the rejection ratio, is kept 103. If this number of datapoints exceeds a certain parameter, this data is bubbled up to either a software agent or an installer to investigate shown 107.

One critical feature of system 100 is taking raw air sensor data and comparing this data to templates to ensure compliance with building regulations and codes. For this, the system 100 requires a large number of templates and requires location coordinates as compliance varies with geographic location. These templates can change from time to time and are edited manually to ensure latest compliance.

Referring next to FIG. 20, an embodiment of a recent code titled Assembly Bill 841 details operation of ventilation systems in schools is shown.

Compliance with code mentioned in FIG. 20 can be automatically checked in real time and the condition of the closed space may be communicated to the building owners via the mobile application. An area inside the closed space 12, may be supplied using the system 100. At the time of installation, the mobile application 37 may request square footage of the area serviced by the monitoring device and the location coordinates, so the right building code templates can be referenced. The $CO_2$ sensor readings from the monitoring device 7 which may be the return air from the closed space and a number of other data points may be used and compared with templates to determine compliance in real time and populate the mobile application accordingly.

In one embodiment, if the $CO_2$ level exceeds 1100 ppm, a plurality of text messages may be sent to indicate failure of compliance and the fan may be turned off and a report may be generated which may also be emailed to the installer for compliance. 1100 ppm is merely taken as example but is not limited to 1100 ppm.

In one embodiment, the real time data from sensors of the monitoring devices may not be sufficient to calculate compliance. To overcome this, suppositions must be made to accurately determine this state of compliance. These suppositions require some Artificial Intelligence algorithms to learn the history of data from sensors, to analyze the data and make decisions based on current and historical data combined with some rule-based decisions.

Other building codes may allow the ventilation system to drop to zero when the space is unoccupied and hence simply comparing $CO_2$ readings may not be sufficient to determine compliance. In one embodiment, a template for occupancy may be required to ensure compliance. This must be learned from $CO_2$ readings, the fan speed and the amount of outside air being used.

The calculation of occupancy from $CO_2$ is a fuzzy as $CO_2$ levels have multiple dependencies. To overcome this, a learning AI algorithm is required to determine occupancy.

Figure 21:
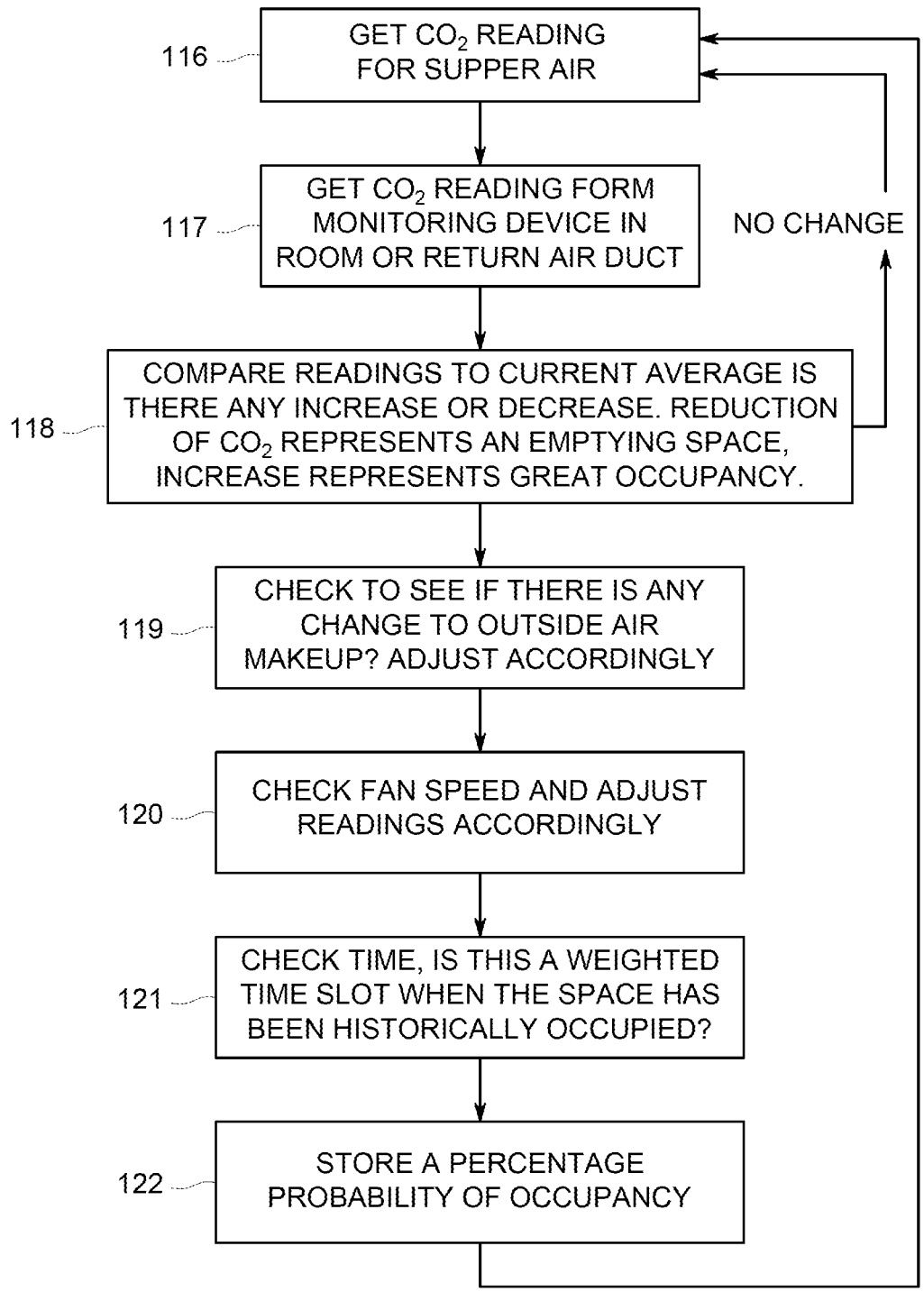
FIG. 21 depicts a flowchart of a learning process in accordance with an embodiment of the present invention.

Referring next to FIG. 21, a flow chart of a learning process. The system 100 reads the level of $CO_2$ being fanned into a closed space 12 at block 116. The return, stale air, is read at block 117. The two values are compared as if there are other sources of fresh air. This comparison may result in the $CO_2$ level of the return air being lower than the supply air. This level is compared to a running average to see if $CO_2$ levels are rising or falling. If the levels are falling, it is important to ensure that it is not just a result of increased fresh air being added to the system at block 119. $CO_2$ levels may also change based on fan speed, so this is taken into account at block 120. Then the rate of change of $CO_2$ is determined. This is now compared against previous periods for this time of day and the day of the week at block 121. A determination is then made based on these values for the likelihood of the occupied space becoming vacant or more occupied. Over a period of several weeks a template is built up which approximates the space occupancy.

In one embodiment, additional inputs, such as an occupancy camera (not shown) are provided which allow a system 100 to be trained to calculate an approximate number of people occupying a space based on the $CO_2$ profile. This can then be used to run the air system to ventilate the space based on the air flow per person which is the most accurate method for expressing healthy spaces. At block 122, a percentage probability of occupancy is stored.

Using the above methods, the system 100 may demonstrate code compliance in real time to the building owners and occupants.

Many building codes require the designers of the HVAC installations to submit data to authorities using compliance software. The system 100 does not provide this type of data, but rather provides a continuous audit on the operations of a previously approved and compliant design.

Referring to FIG. 22 an embodiment of a pressing button 78 is shown. A building owner with superior credentials will be presented with a summary of the local building regulations. The local building codes based on GPS coordinates are loaded. Where a code can be proven by performance, the required template result is posted as a simple check mark 124.

Modern building heating and ventilation systems are complex. To commission and test systems is expensive and time consuming and is hence not always done correctly. The system 100 performs these tests automatically and continuously reducing the cost of ownership and the cost of compliance. Using the AI powered templates, it is possible to change the operations of the monitoring devices so that they automatically to respond to changes in the building codes and guidelines. Owing to Covid 19 outbreak, the time a system 100 (or monitoring devices) should run prior to occupancy was 90 minutes. This changed to 120 minutes along with the preferred amounts of outside air usage. The analysis from the system 100 sees the changes in the cloud templates and reprograms the operations of the monitoring devices to comply.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed but could have additional steps not included in the figure. A process may correspond to a method, a function, a procedure, a subroutine, a subprogram, etc. When a process corresponds to a function, its termination corresponds to a return of the function to the calling function or the main function.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

In the embodiments described above, for the purposes of illustration, processes may have been described in a particular order. It should be appreciated that in alternate embodiments, the methods may be performed in a different order than that described. It should also be appreciated that the methods and/or system components described above may be performed by hardware and/or software components (including integrated circuits, processing units, and the like), or may be embodied in sequences of machine-readable, or computer-readable, instructions, which may be used to cause a machine, such as a general-purpose or special-purpose processor or logic circuits programmed with the instructions to perform the methods. Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data. These machine-readable instructions may be stored on one or more machine-readable mediums, such as CD-ROMs or other type of optical disks, solid-state drives, tape cartridges, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

The methods, systems, devices, graphs, and tables discussed herein are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

While illustrative and presently preferred embodiments of the disclosed systems, methods, and machine-readable media have been described in detail herein, it is to be understood that the inventive concepts may be otherwise variously embodied and employed, and that the appended claims are intended to be construed to include such variations, except as limited by the prior art. While the principles of the disclosure have been described above in connection with specific apparatuses and methods, it is to be clearly understood that this description is made only by way of example and not as limitation on the scope of the disclosure.

What is claimed is:

1. A system for monitoring air quality of a closed space, the system comprising:
    a plurality of monitoring devices; and
    a plurality of ducts, wherein:
        the plurality of ducts are coupled with the closed space,
        the plurality of monitoring devices are configured to monitor a quality of air inside the plurality of ducts,
        each of the plurality of monitoring devices stores a location of placement of each of a monitoring device present inside the closed space, and the plurality of monitoring devices are configured to:
  learn a level of carbon dioxide present inside the closed space over a period of time;
  estimate a number of occupants present inside the closed space based on the level of carbon dioxide present inside the closed space over the period of time using a machine learning model; and
  transmit the monitored quality of air inside the closed space along with the location of the placement of each of the monitoring device and the identified number of occupants present inside the closed space to a cloud server.

2. The system for monitoring the air quality of the closed space as recited in claim 1, wherein each of the plurality of monitoring devices is further configured to:
  adjust the quality of air inside the closed space based on the monitored quality of air inside the closed space and the identified number of occupants present inside the closed space to the cloud server using the machine learning model.

3. The system for monitoring the air quality of the closed space as recited in claim 1, further comprising:
  a plurality of computing devices communicatively coupled with the cloud server, and comprising:
  a display;
  a processor coupled to the display and configured to:
    display the quality of air along with a location of the plurality of monitoring devices, wherein the number of occupants present inside the closed space; and
    allow a plurality of users to access the cloud server, the cloud server is configured to:
      adjust the quality of air inside the closed space by:
        adjusting a plurality of parameters relating to air quality, wherein the plurality of parameters comprise speed of air entering the closed space, a temperature of the closed space, a humidity of air present inside the closed space, the level of carbon dioxide levels in the closed space, and
adjusting a level of Total Volatile Organic Compounds (TVOC) pollutants inside the closed space, quality of an air filter present inside the closed space.

4. The system for monitoring the air quality of the closed space as recited in claim 1, wherein the plurality of monitoring devices are further configured to connect to the cloud server using a wireless network.

5. The system for monitoring the air quality of the closed space as recited in claim 1, wherein the plurality of monitoring devices are further configured to:
  change the air inside the closed space and adjust a speed of a fan present inside the closed space based on the level of carbon dioxide present inside the closed space.

6. The system for monitoring the air quality of the closed space as recited in claim 1, further comprising:
  an occupancy camera, wherein the occupancy camera is configured to estimate a number of users present inside the closed space;
  wherein the number of occupants is detected inside the closed space based on the occupancy camera and the level of carbon dioxide present inside the closed space.

7. The system for monitoring the air quality of the closed space as recited in claim 1, wherein the plurality of monitoring devices are configured to be reprogrammed according to air quality guidelines of the closed space.

8. The system for monitoring the air quality of the closed space as recited in claim 1, wherein each of the plurality of monitoring devices is powered by a 24 volts AC supply.

9. A method for remotely monitoring air quality of a closed space, the method comprising:
  providing a plurality of monitoring devices;
  providing a plurality of ducts; wherein:
    the plurality of ducts are coupled with the closed space, the plurality of monitoring devices perform the following steps:
      monitoring a quality of air inside the plurality of ducts;
      learning a level of carbon dioxide present inside the closed space over a period of time;
      estimating a number of occupants present inside the closed space based on a level of carbon dioxide present inside the closed space over the period of time using a machine learning model; and
      transmitting the monitored quality of air inside the closed space along with the location of placement of each of a monitoring device and identified number of occupants present inside the closed space to a cloud server.

10. The method for remotely monitoring the air quality of the closed space as recited in claim 9, wherein each of the plurality of monitoring devices further performs the steps of:
  adjusting the quality of air inside the closed space based on the transmitted monitored quality of air inside the closed space and identified number of occupants present inside the closed space to the cloud server using the machine learning model.

11. The method for remotely monitoring the air quality of the closed space as recited in claim 9, further comprising:
  a plurality of computing devices communicatively coupled with the cloud server, wherein the plurality of computing devices perform the following steps:
    displaying the quality of air along with a location of the plurality of monitoring devices;
    displaying number of occupants present inside the closed space;
    allowing a plurality of users to access the cloud server,
    adjusting the quality of air inside the closed space by:
      adjusting one or more parameters relating to air quality, wherein the one or more parameters comprises speed of air entering the closed space, temperature of the closed space, humidity of air present inside the closed space, the level of carbon dioxide levels in the closed space; and
      adjusting level of Total Volatile Organic Compounds (TVOC) pollutants inside the closed space, quality of an air filter present inside the closed space.

12. The method for remotely monitoring the air quality of the closed space as recited in claim 9, further comprising connecting the plurality of monitoring devices to the cloud server using a wireless network.

13. The method for remotely monitoring the air quality of the closed space as recited in claim 9, wherein the plurality of monitoring devices further performs the step of:
  changing air inside the closed space and adjust a speed of a fan present inside the closed space based on the level of carbon dioxide present inside the closed space.

14. The method for remotely monitoring the air quality of the closed space as recited in claim 9, further comprising:
  estimating a number of users present inside the closed space using an occupancy camera, wherein the number of occupants is detected inside the closed space based on the occupancy camera and the level of carbon dioxide present inside the closed space.

15. The method for remotely monitoring the air quality of the closed space as recited in claim 9, further comprising:

reprogramming the plurality of monitoring devices according to air quality guidelines of the closed space.

16. The method for remotely monitoring the air quality of the closed space as recited in claim 9, further comprising:
powering each of the plurality of monitoring devices by a 24 volts AC supply.

17. A non-transitory computer-readable medium having instructions stored thereon, wherein the instructions, when executed by one or more processors of an air quality monitoring system, cause the air quality monitoring system to:
provide a plurality of monitoring devices;
provide a plurality of ducts; wherein:
the plurality of monitoring devices perform the following steps to:
monitor a quality of air inside the plurality of ducts;
learn a level of carbon dioxide present inside the closed space over a period of time;
estimate a number of occupants present inside the closed space based on a level of carbon dioxide present inside the closed space over the period of time using a machine learning model; and
transmit the monitored quality of air inside the closed space along with the location of placement of each of a monitoring device and identified number of occupants present inside the closed space to a cloud server.

18. The non-transitory computer-readable medium as recited in claim 17, wherein each of the plurality of monitoring devices further performs the steps to:
adjust the quality of air inside the closed space based on the transmitted monitored quality of air inside the closed space and identified number of occupants present inside the closed space to the cloud server using the machine learning model.

19. The non-transitory computer-readable medium as recited in claim 17, wherein the air quality monitoring system further comprises:
a plurality of computing devices communicatively coupled with the cloud server, wherein the plurality of computing devices perform the following steps to:
display the quality of air along with a location of the plurality of monitoring devices;
display number of occupants present inside the closed space;
allow a plurality of users to access the cloud server,
adjust the quality of air inside the closed space by adjusting one or more parameters relating to air quality, wherein the one or more parameters comprises speed of air entering the closed space, temperature of the closed space, humidity of air present inside the closed space, the level of carbon dioxide levels in the closed space; and
adjust level of Total Volatile Organic Compounds (TVOC) pollutants inside the closed space, quality of an air filter present inside the closed space.

20. The non-transitory computer-readable medium as recited in claim 17, wherein the plurality of computing devices perform the steps to connect the plurality of monitoring devices to the cloud server using a wireless network.

* * * * *